United States Patent [19]

Tatum

[11] Patent Number: 5,595,192
[45] Date of Patent: Jan. 21, 1997

[54] RESTRAINING GARMENT FOR SURGICAL PATIENTS

[76] Inventor: Eugene T. Tatum, 1617 Euclid Ave., Bowling Green, Ky. 42103

[21] Appl. No.: 659,392

[22] Filed: Jun. 6, 1996

[51] Int. Cl.⁶ .................................................. A61B 19/00
[52] U.S. Cl. ...................... 128/869; 128/875; 128/876; 5/424
[58] Field of Search .................................. 128/845, 846, 128/869–876; 5/648, 650, 424, 494, 658

[56] References Cited

U.S. PATENT DOCUMENTS

| | | |
|---|---|---|
| 3,566,864 | 3/1971 | Garrow ..................................... 128/874 |
| 3,580,523 | 5/1971 | Preston . |
| 3,641,997 | 2/1972 | Posey, Jr. . |
| 3,741,200 | 6/1973 | Morin . |
| 3,814,414 | 6/1974 | Chapa . |
| 3,844,550 | 10/1974 | McGuire . |
| 3,897,778 | 8/1975 | Forbes-Robinson et al. . |
| 3,901,229 | 8/1975 | Hensel et al. . |
| 3,982,742 | 9/1976 | Ford . |
| 4,050,737 | 9/1977 | Jordan . |
| 4,122,587 | 10/1978 | Weiss et al. . |
| 4,360,014 | 11/1982 | Manahan ................................. 128/874 |
| 4,373,709 | 2/1983 | White . |
| 4,524,768 | 6/1985 | Serrao . |
| 4,549,540 | 10/1985 | Caspari et al. . |
| 4,608,969 | 9/1986 | Hamlin . |
| 4,618,973 | 10/1986 | Lasky . |
| 4,678,186 | 7/1987 | McIntyre et al. . |
| 4,860,771 | 8/1989 | Burgos ..................................... 128/876 |
| 4,890,604 | 1/1990 | Nelson . |
| 4,911,105 | 3/1990 | Hocum ..................................... 128/875 |
| 4,911,106 | 3/1990 | Goodwin . |
| 4,913,413 | 4/1990 | Raab . |
| 4,995,378 | 2/1991 | Dyer et al. . |
| 5,076,288 | 12/1991 | Millard et al. . |
| 5,133,741 | 7/1992 | Filho . |
| 5,190,055 | 3/1993 | O'Connor . |
| 5,400,803 | 3/1995 | Vines . |
| 5,433,222 | 7/1995 | Boomgaarden et al. . |
| 5,456,655 | 10/1995 | Morris . |
| 5,524,306 | 6/1996 | George ..................................... 5/424 |

*Primary Examiner*—Michael A. Brown
*Attorney, Agent, or Firm*—Wheat, Camoriano, Smith & Beres, PLC

[57] ABSTRACT

A restraining garment used with a patient supinely positioned on a tilted operating table has a pair of wrap members that wrap about the upper thighs of the patient adjacent the groin area thereby providing operating access to the entire anterior torso of the supinely positioned patient. The underside of the garment is secured to the operating table and prevents the patient from sliding down the table due to the severe tilt of the table.

9 Claims, 3 Drawing Sheets

5,595,192

RESTRAINING GARMENT FOR SURGICAL PATIENTS

BACKGROUND OF THE INVENTION

This invention relates to devices used to secure a patient to an operating table and, more particularly, to a restraining garment used to prevent a patient from sliding on an operating table tilted to facilitate the operation.

In many surgeries, it is desirable to have the patient's head elevated above the feet. Examples of such surgeries are various types of stomach surgery, duodenal surgery, colon resection, splenectomy, and Nissen fundoplication. Many of the mentioned surgeries may be performed using the laparoscopic method, which entails making small incisions in a patient's abdomen for the insertion of a fiber optic tube and long-handled laparoscopic instruments. An impediment to successful surgeries using laparoscopic methods, particularly in the upper abdomen, is that abdominal contents, such as the folds of the intestines, tend to get in the way. Tilting of the operating table to position the patient's head well above the feet is particularly helpful in minimizing these visual obstructions.

The problem of tilting an operating table to an angle with the horizontal sufficient to avoid the aforementioned visual obstructions is that the cohesion between the patient and the operating table is not sufficient to prevent the patient from sliding down the table. The prior art, while replete with medical devices for securing patients to various objects such as beds, stretchers, wheel chairs, and operating tables, has not focussed to any great extent on this problem. The prior art restraints or securing devices range from belts, straps and harnesses to garments. U.S. Pat. No. 5,211,186 issued to Shoemaker is typical of those patents describing personnel immobilizing straps and belts. Other patents directed to similar inventions are U.S. Pat. No. 5,433,222 to Boomgarten et. al., U.S. Pat. No. 4,744,354 to Triunfol, U.S. Pat. No. 4,524,768 to Serrao, and U.S. Pat. No. 5,190,055 to O'Connor. These patents all disclose constructions designed primarily to inhibit thrashing movements of the patients and are too cumbersome and/or restrictive for surgical applications.

One U.S. Pat. No. 5,400,803 to Vines discloses a structure for supporting a supine patient on a tilted surface that comprises a diaper shaped body supporting member that includes a torso portion, a crotch portion and a base sheet. It is clear that the torso portion would cover the lower anterior abdomen and anterior pelvis, both common sites of surgery or surgical field preparation. Surgical applications would apparently be limited to the upper two-thirds of the torso. Moreover, the crotch portion would preclude obstetrical applications or easy usage of bladder catheters.

From the above, it can be seen that the prior art patents have not adequately addressed the problems associated with significantly tilted surgical tables. It is therefore a primary object of the present invention to provide for a surgical restraining garment which secures the pelvis and upper thighs to an operating table in such a way as to prevent sliding of the patient's torso when the table is tilted Another object of the present invention is to provide a surgical restraining garment which is simple in structure and easy to use, thus minimizing pre-operative set-up time.

Still another object of the present invention is to provide a surgical restraining garment which does not wrap around the anterior chest, abdomen, or anterior pelvis, so as to provide operating personnel unobstructed access to these areas.

A further object of the present invention is to provide a surgical restraining garment which does not cover the external genitalia, so as to provide operating personnel unobstructed access for possible gynecologic or obstetrical applications or usage of a bladder catheter.

SUMMARY OF THE INVENTION

The present invention pertains to a surgical restraining garment which comprises a back member with means for securely attaching the garment to an operating table and right and left upper thigh wrap members. The back member wraps around the lower back and buttocks of the supine patient and is connected to the right and left upper thigh wrap members. Each of the upper thigh wrap members is comprised of two portions, a lateral portion and a medial portion. The lateral portion wraps about the lateral hip area and extends diagonally and inferiorly around the anterolateral upper thigh. The medial portion wraps about the medial upper thigh near the groin and extends diagonally and superiorly across the anteromedial upper thigh. The lateral and medial portions of the right and left upper thigh wraps are brought together and attached to one another by operatively compatible fasteners secured at or near the distal ends of the wraps. The means of securing the garment itself to the operating table may be any one of several types, including (but not limited to) a broad belt attached to the back member which may be wrapped around the operating table and buckled or attached by loops or ties to the operating table.

DETAILED DESCRIPTION OF THE PREFERRED EMBODIMENT

Figure 1:
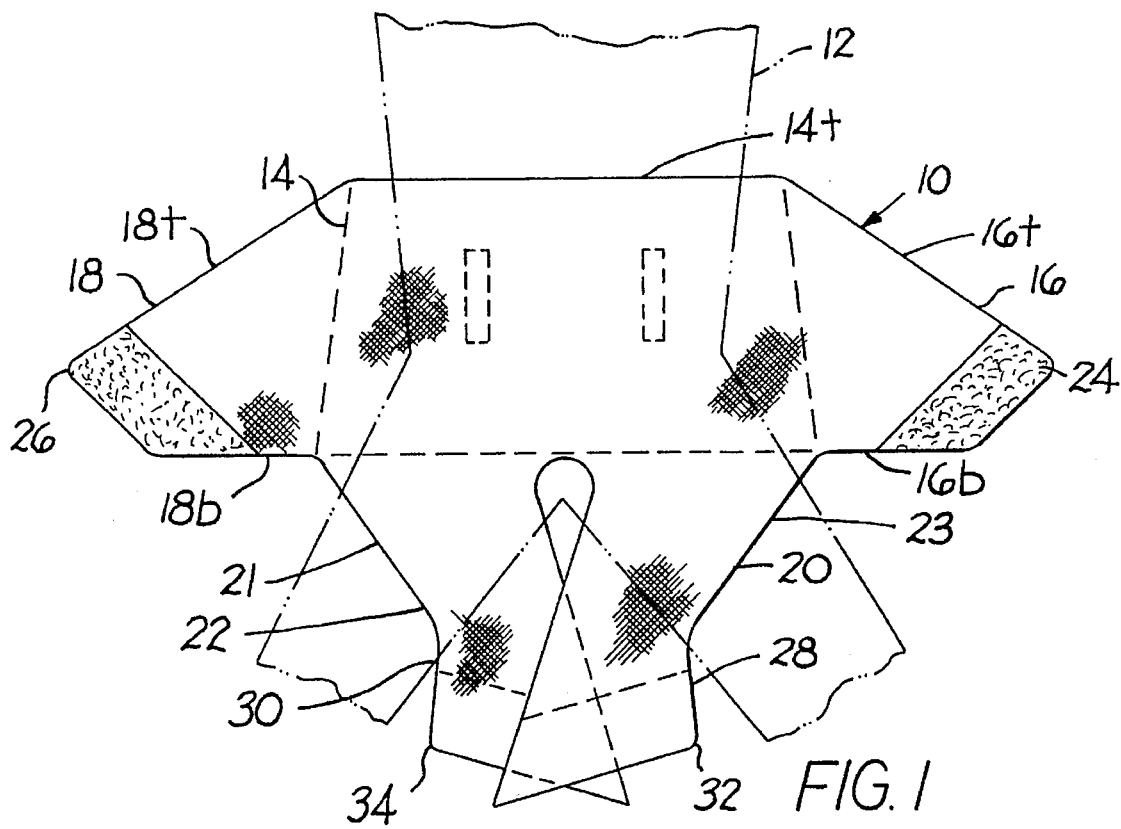
FIG. 1 is a top view of a restraining garment of the present invention spread flat on a support surface such as an operating table showing, in dashed lines, the lower torso and thighs of a supinely positioned patient properly positioned on the garment.

In FIG. 1, a garment according to the present invention, shown generally by the character numeral 10, is laid flat over a support surface (not shown) such as the surface of a operating table. This is in preliminary preparation for placing a patient in a supine position directly over the garment 10. When the garment is laid flat, as shown in FIG. 1, and fastened to the operating table in a manner discussed below, the patient (illustrated in phantom by dashed lines 12) is positioned over the garment 10 with the lower back and buttocks in contact with a centrally disposed region 14 enclosed by dashed lines and top edge 14t. While the garment is an integral piece of fabric, for sake of clarity, the region 14 may be defined as that portion of the garment 10 located between a pair of left and right lateral portions or "arms" 16 and 18 and a pair of left and right downwardly extending medial portions or "legs" 20 and 22. Left and right, for purposes of this description, are the left and right directions as seen by a supine patient. Arms 16 and 18 have converging top and bottom sides illustrated, respectively, as 16t, 16b and 18t, 18b which collectively define a generally downwardly inclined shape to each of the arms 16, 18 with respect to the horizontally disposed top 14t of the central region 14. Positioned at or near the distal ends of the arms 16 and 18 are fastener elements 24 and 26, respectively, that may be one set of a hook and loop fastener operatively compatible with a second set of fasteners 32 and 34 described below.

Legs 20 and 22 are "bowlegged" in the sense that, at the boundary area with the central region 14, the legs 20 and 22 are spaced from each other but generally converge toward one another and overlap at the distal ends thereof or "feet" 28 and 30. Each of the feet 28 and 30 are provided with fastener elements 32 and 34 that may be the other set of a hook and loop fastener and thus can be cooperatively fastened to respective fastener elements 24 and 26. The outside edges 23 and 21 of respective legs 20 and 22 from the boundary of the central region of arms 16 and 18 to the feet 28 and 30 define an area over which the thighs of the patient may be initially placed and spread as illustrated in FIG. 1.

Figure 2:
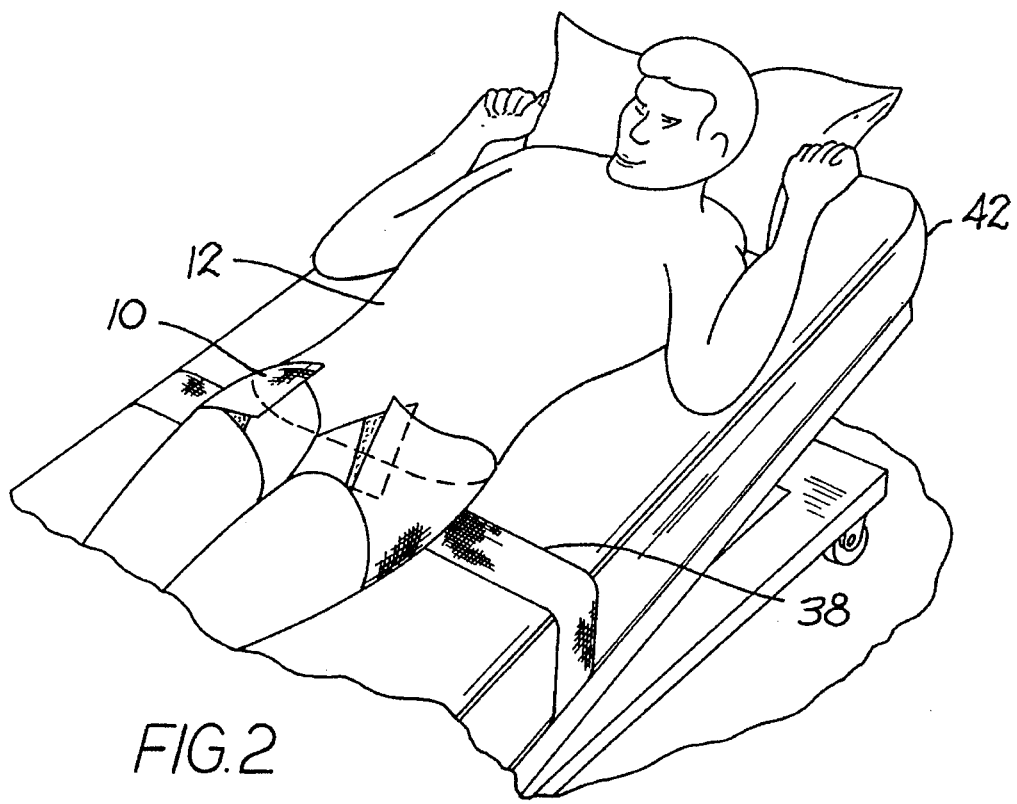
FIG. 2 is a perspective view of a supinely positioned patient restrained by the garment of the present invention and lying on a support surface of an operating table inclined so that the patient's head is above the feet.
Figure 3:
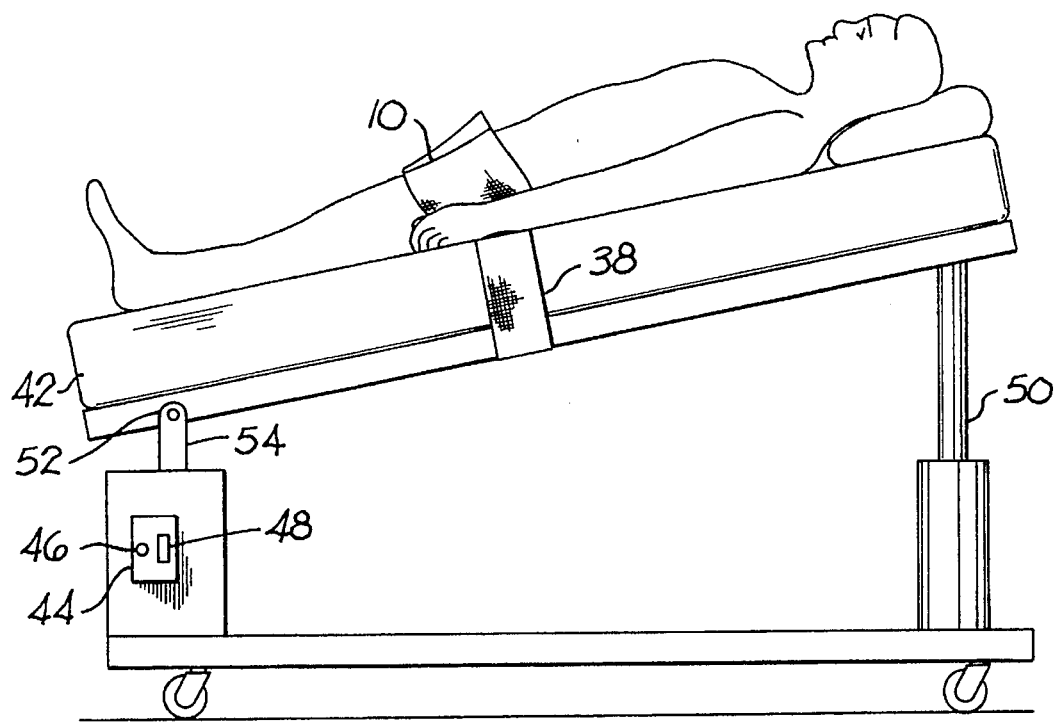
FIG. 3 is a side elevation of the patient, garment and operating table shown in FIG. 2.
Figure 4:
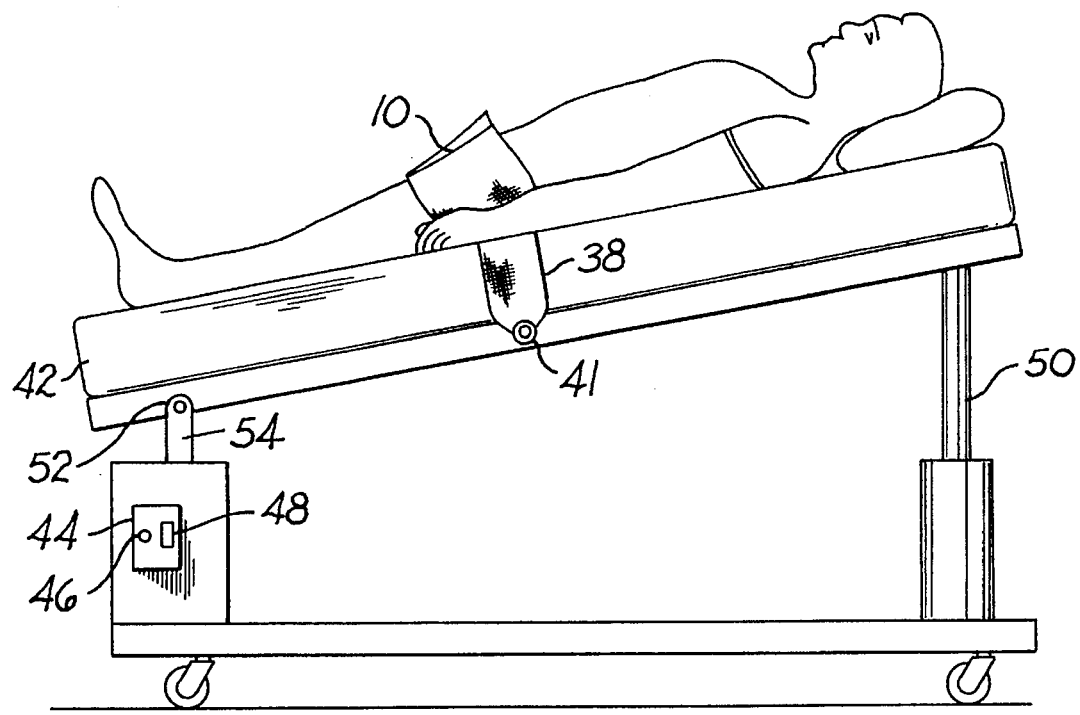
FIG. 4 is a side elevation similar to that shown in FIG. 3 with a modified belt attachment to the operating table.

When a patient is in place over the garment 10, the arms and legs thereof can be folded or wrapped about the upper thighs of the patient. Central region 14 wraps about the lower back and buttocks of the patient while the arms 16 and 18 wrap in a diagonal and inferior (or downward) direction about the anterolateral upper thigh. The legs 20 and 22 are wrapped about the medial thigh near the groin area and extend diagonally and superiorly, i.e., in an upwardly direction, about the anteromedial upper thigh to meet, respectively, the downwardly wrapped arms 16 and 18. The fastener elements 24 and 26 at the ends of respective arms 16 and 18 then can be secured to respective fastener elements 32 and 34 at the ends of respective legs 20 and 22. It should be noted from FIG. 2 that the garment 10, when wrapped and secured about the patient, provides access to the surgical team to the entire anterior torso of the patient, including the genital area. The restraint of the garment is limited solely to the upper thighs and provides particular resistance to sliding of the patient down the table when inclined so that the patient's head is above the feet. As stated before, this positioning of the patient is desirable for many types of surgeries including, but not limited to, laparoscopic surgery. The particular means for tilting the operating table 42 as illustrated in FIGS. 2, 3 and 4 is not described in any detail since it plays no role in the present invention. However, the table 42 could be a hydraulic or electrically operated table controlled by panel 44 that includes an off-on power switch 46 and a raise-lower rocker switch 48. One end table 42 is raised by movement of piston or bracket 50 with the other end pivoting around pivot connection 52 connected to stationary stanchion 54.

Figure 5:
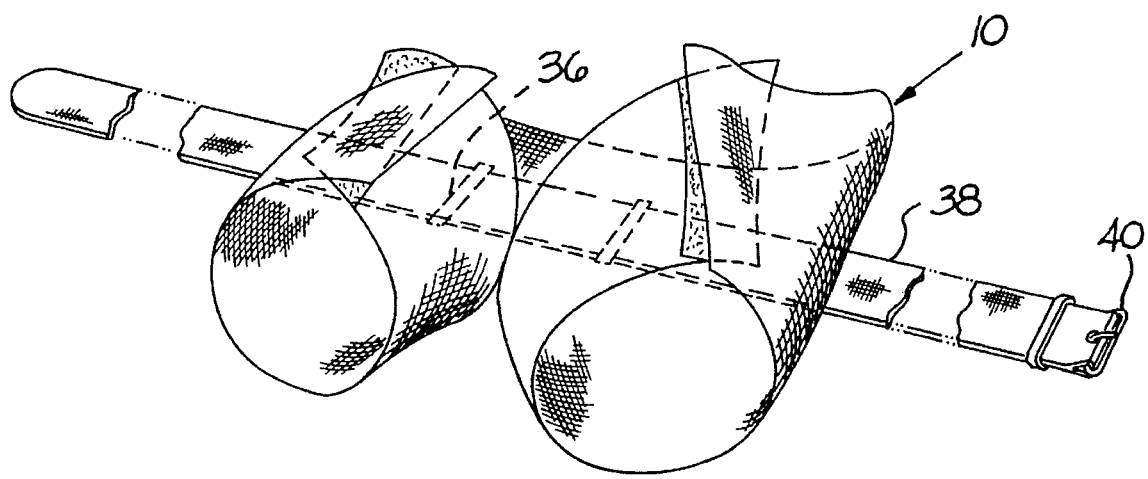
FIG. 5 is a perspective view of the restraining garment shown in the wrapped state without the patient for clarity.
Figure 6:
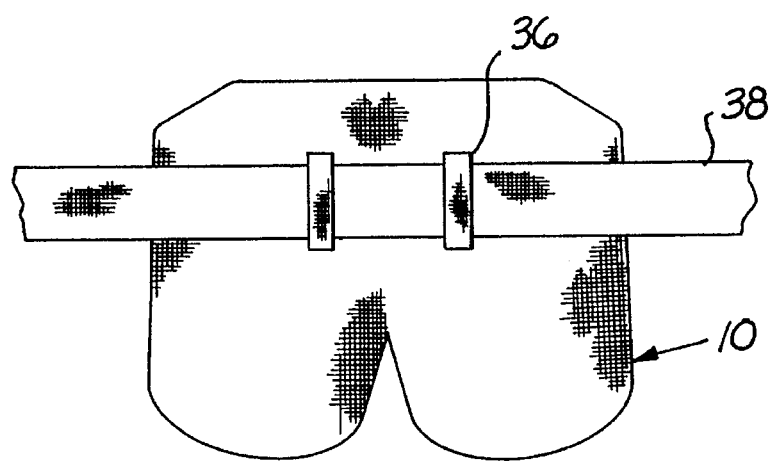
FIG. 6 is a bottom view of the garment shown in FIG. 5 to illustrate one possible way of connecting the garment to the belt.

The relationships of various parts of the garment 10 when wrapped is perhaps more clearly illustrated by FIG. 5 showing a perspective of the wrapped garment without the lower torso and thighs of the patient. It should also be noted that the garment 10 may be supplied with a pair of loops 36 attached to the back of the garment in the central region 14 as shown in FIG. 6 through which a belt 38 can be passed. Belt 38 then may be buckled beneath the operating table via a buckle 40, as illustrated in FIG. 3, or fastened through a snap or loop attachment 41 as shown in FIG. 4. Alternatively, garment 10 may be provided with a broad belt 38 which is permanently fixed to the back of the central region 14, the belt then being secured to the operating table by any of the fastener devices described above.

From a reading of the above, it is clear that the objectives previously set forth have been met. Additional modifications and variations will become evident to those with ordinary skill in the art without departure from the spirit and scope of the appended claims.

I claim:

1. A garment for restraining the sliding movement of a patient's body down an inclined operating table comprising
    a back member positioned between the lower back and buttocks of a patient and an operating table, said back member having fastener means attached thereto for securing said garment to said table,
    left and right upper thigh wrap members connected to said back member which, when said garment is in use, are wrapped and secured about the upper thighs of said patient,
    said left and right upper thigh wrap members each comprising a lateral portion and a medial portion associated with the left and right thighs of said patient,
    when said garment is in use,
        each of said lateral portions being wrapped about a respective associated lateral hip area and extending diagonally and inferiorly across a respective anterolateral upper thigh and
        each of said medial portions being wrapped across a respective associated medial thigh adjacent the groin and extending diagonally and superiorly across a respective anteromedial upper thigh and overlapping an end of a respective lateral portion, each end of said lateral and medial portions having operatively compatible fasteners for securing each of said thigh wrap members about said respective thigh.

2. The garment of claim 1 including loops secured to the back side of said back member and a belt passing through said loops and adapted to be secured directly to the operating table.

3. The garment of claim 1 including a belt secured to a back side of said back member and adapted to be secured to the operating table.

4. The garment of claim 3 in which said belt is releasably secured to said back member.

5. A restraining garment releasably connected to an operating table for restraining sliding movement of a supine patient on the operating table when inclined, said garment having a shape adapted to be releasably wrapped and secured about the buttocks, lower back and upper thighs of the patient and providing access by medical personnel to essentially the entire anterior torso of the supine patient's body, including the groin area, said garment when laid flat on the operating table comprising
    a centrally disposed region adapted to be positioned beneath the buttocks and lower back of a supinely positioned patient and fastened to the operating table the ready position,
    left and right arm members extending from said centrally disposed region and having distal ends each mounting a first complementary element of a fastener,
    said arm members extending in a downwardly direction so that when said centrally disposed region is in the ready position said arm members can be wrapped around the anterolateral upper thigh of the supinely positioned patient in a diagonal and inferior direction, and left and right leg members connected to said central region and each extending substantially downwardly therefrom and having a foot mounting a second element of said fastener, said leg members being bowlegged and spaced from each other where connected to said central region but overlapping one another near said feet, said left and right leg members having outside edges converging toward each other from said upper arm members to said leg distal ends and when said central region is in the ready position, being positioned beneath the upper thighs of the supinely positioned patient so that said left and right lower leg members can be wrapped about respective anteromedial upper thighs of said patient in a diagonal and superior direction towards said respective left and right upper arms members and fastened thereto by cooperative fastening interaction of said first and second fastening elements.

6. A garment for restraining the movement of a patient's body in combination with an operating table having means for inclining the patient support surface of said table at a predetermined angle to the horizontal, said garment further comprising a back member positioned between the lower back and buttocks of a patient and an operating table, said back member having fastener means attached thereto for securing said garment to said table, left and right upper thigh wrap members connected to said back member which, when said garment is in use, are wrapped and secured about the upper thighs of said patient, said left and right upper thigh wrap members each comprising a lateral portion and a medial portion associated with the left and right thighs of said patient, when said garment is wrapped about the supinely positioned patient, each of said lateral portions being wrapped about a respective lateral lip area and extending diagonally and inferiorly across a respective anterolateral upper thigh and each of said medial portions being wrapped about a respective medial thigh adjacent the groin and extending diagonally and superiorly across a respective anteromedial upper thigh and overlapping an end of a respective lateral portion, each end of said lateral and medial portions having operably compatible fasteners for securing said ends of said left and right medial portions to respective ends of said left and right lateral portions.

7. The combination of claim 6 in which the fastening means includes a plurality of loops secured to a back side of said garment and a belt passing through said loops and releasably secured at the distal ends thereof beneath said operating table.

8. The combination of claim 6 in which the fastening means includes a plurality of loops secured to said garment and a belt passing through said loops and releasably secured to the sides of said operating table.

9. The combination of claim 6 including at least one belt secured to said garment and releasably secured at distal ends thereof to said operating table.

* * * * *